(12) United States Patent
Barrett et al.

(10) Patent No.: US 12,059,519 B2
(45) Date of Patent: Aug. 13, 2024

(54) SYSTEMS AND METHODS FOR MEASURING ELECTRICAL CHARACTERISTIC OF MEDICAL FLUIDS

(71) Applicant: Fresenius Medical Care Holdings, Inc., Waltham, MA (US)

(72) Inventors: Louis Leegrande Barrett, WestPoint, UT (US); Jon F. Moss, Antioch, CA (US); David W. Peterson, Clinton, UT (US); Ronald S. Glaittli, Bountiful, UT (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 246 days.

(21) Appl. No.: 17/545,543

(22) Filed: Dec. 8, 2021

(65) Prior Publication Data
US 2022/0218888 A1 Jul. 14, 2022

Related U.S. Application Data

(60) Provisional application No. 63/135,960, filed on Jan. 11, 2021.

(51) Int. Cl.
*A61M 1/28* (2006.01)

(52) U.S. Cl.
CPC ..... *A61M 1/287* (2013.01); *A61M 2205/3327* (2013.01); *A61M 2205/35* (2013.01)

(58) Field of Classification Search
CPC .......... A61M 1/287; A61M 2205/3327; A61M 2205/35; G01N 27/08; G01N 27/045
See application file for complete search history.

(56) References Cited

U.S. PATENT DOCUMENTS

| 3,365,659 A | 1/1968 | Wolfram |
| 3,965,414 A | 6/1976 | Teass, Jr. |

(Continued)

FOREIGN PATENT DOCUMENTS

| CN | 203923708 | 11/2014 |
| CN | 107860799 | 3/2018 |

(Continued)

OTHER PUBLICATIONS

International Preliminary Report on Patentability in International Appln. No. PCT/US2021/062361, mailed Jul. 20, 2023, 8 pages.

(Continued)

*Primary Examiner* — Christopher P McAndrew
*Assistant Examiner* — Zannatul Ferdous
(74) *Attorney, Agent, or Firm* — Fish & Richardson P.C.

(57) ABSTRACT

A circuit for measuring the conductivity of a medical fluid, the circuit comprising: a data collecting cell through which a medical fluid is configured to flow; an input voltage source that provides an input voltage to the data collecting cell; a voltage measurement unit configured to measure the input voltage and an output voltage of the data collecting cell; and a switch in communication with the voltage measurement unit, the switch configured to switch between a first state in which the voltage measurement unit is configured to measure the input voltage and a second state in which the voltage measurement unit is configured to measure the output voltage of the data collecting cell.

16 Claims, 5 Drawing Sheets

(56) References Cited

U.S. PATENT DOCUMENTS

| | | | |
|---|---|---|---|
| 4,808,930 A | 2/1989 | Kaiser | |
| 4,808,931 A | 2/1989 | Ling | |
| 5,008,627 A | 4/1991 | Tsutsuta et al. | |
| 5,583,432 A | 12/1996 | Barnes | |
| 5,708,363 A * | 1/1998 | Yates | G01R 27/22 324/707 |
| 6,690,172 B2 | 2/2004 | Higo | |
| 2003/0059945 A1* | 3/2003 | Dzekunov | C12N 15/87 435/461 |
| 2004/0254513 A1* | 12/2004 | Shang | A61M 1/3659 210/746 |
| 2006/0133176 A1* | 6/2006 | Kim | G11C 5/145 365/226 |
| 2006/0275907 A1 | 12/2006 | Glocker | |
| 2006/0275917 A1 | 12/2006 | Glocker | |
| 2007/0024287 A1 | 2/2007 | Graves et al. | |
| 2011/0154910 A1 | 6/2011 | Murata | |
| 2013/0213891 A1 | 8/2013 | Karoor | |
| 2013/0271149 A1 | 10/2013 | Lord, III et al. | |
| 2014/0112828 A1* | 4/2014 | Grant | A61M 1/3643 210/232 |
| 2017/0173262 A1* | 6/2017 | Veltz | G16H 20/17 |
| 2017/0182235 A1 | 6/2017 | Weaver et al. | |
| 2017/0216512 A1 | 8/2017 | Kopperschmidt | |
| 2018/0278050 A1 | 9/2018 | Rabier | |
| 2020/0393395 A1 | 12/2020 | James et al. | |
| 2024/0060924 A1 | 2/2024 | James et al. | |

FOREIGN PATENT DOCUMENTS

| | | |
|---|---|---|
| EP | 2143378 | 1/2010 |
| GB | 1517697 | 7/1978 |
| GB | 2064779 | 6/1981 |
| KR | 10-2009-0129577 | 12/2009 |
| RU | 2597067 | 9/2016 |
| WO | WO 93/18395 | 9/1993 |
| WO | WO 00/27199 | 5/2000 |

OTHER PUBLICATIONS

International Search Report and Written Opinion in Appln. No. PCT/US2021/062361, mailed Mar. 18, 2022, 15 pages.

Keim, "Measuring Resistance, In Circuit and Out-Technical Articles," Jun. 21, 2015, retrieved on Oct. 25, 2019, retrieved from URL <https://www.allaboutcircuits.com/technical-articles/measuring-resistance-in-circuit-and-out/>, 4 pages.

[No. Author Listed] [online], "Pogo Pins in Action," Posted on Aug. 6, 2013, retrieved on Mar. 2, 2022, <https://www.youtube.com/watch?v=XfxvxwSIjrU>, 1 page [Video Submission].

[No. Author Listed] [online], "Swift-Dock-spring loaded interface assemblies for docking stations," Posted on Oct. 11, 2016, retrieved on Mar. 2, 2022, <https://www.youtube.com/watch?v=1K7RkjL87Dg>, 1 page [Video Submission].

Sharp et al., "Tissue type determination by impedance measurement: A bipolar and monopolar comparison," Saudi J Anaesth., Jan.-Mar. 2017, 11(1): 15-20.

* cited by examiner

SYSTEMS AND METHODS FOR MEASURING ELECTRICAL CHARACTERISTIC OF MEDICAL FLUIDS

TECHNICAL FIELD

This invention relates to measuring conductivity of a medical fluid.

BACKGROUND

During hemodialysis, impurities and toxins are removed from the blood of a patient by drawing the blood out of the patient through a blood access site, typically via a catheter, and then passing the blood through an artificial kidney (often referred to as a "dialyzer"). The artificial kidney includes a semi-permeable membrane that separates a first conduit from a second conduit. Generally, a dialysis solution (often referred to as a "dialysate") flows through the first conduit of the dialyzer while the patient's blood flows through the second conduit of the dialyzer, causing impurities and toxins to be transferred from the blood to the dialysate through the semi-permeable membrane. The impurities and toxins can, for example, be removed from the blood by a diffusion process. After passing through the dialyzer, the purified blood is then returned to the patient.

Maintaining a substantially constant concentration of sodium in the patient's blood throughout the hemodialysis treatment can help to reduce or prevent discomfort experienced by the patient. Therefore, sodium concentrations in the patient's blood can be modified through the level of sodium in the dialysate which requires this level to be monitored during hemodialysis treatment.

SUMMARY

Implementations of the present disclosure are directed to a device for measuring electrical characteristics of medical fluids, such as sodium in the dialysate solution.

In an aspect, a circuit for measuring the conductivity of a medical fluid includes a data collecting cell through which a medical fluid is configured to flow, an input voltage source that provides set input voltage to the data collecting cell, a voltage measurement unit configured to measure the input voltage and an output voltage of the data collecting cell, and a switch in communication with the voltage measurement unit. The switch is configured to switch the voltage measurement unit between a first state in which it is configured to measure the input voltage and a second state in which the voltage measurement unit is configured to measure the output voltage of the data collecting cell.

Implementations can include one or more of the following features.

In some implementation, a cell voltage is determined by taking a difference between the input voltage and the output voltage.

In some implementations, a cell current is determined by measuring a current through a resistor connected in series with the output of the data collecting cell.

In some implementations, a cell conductance is determined by dividing the cell current by the cell voltage.

In some implementations, the conductivity of the medical fluid flowing through the data collecting cell is determined by multiplying the cell conductance by a cell constant.

In some implementations, the cell constant is determined by measuring one or more conductivities of known solutions by the circuit.

In some implementations, the cell constant is pre-calibrated such that the cell constant is known before the conductivity of the medical fluid is measured.

In some implementations, a precise calibration of the voltage measurement unit is not required to provide an accurate measurement of the cell conductance.

In some implementations, the input voltage source operates at a frequency of about 100 kHz.

In some implementations, the input voltage source can operate at other frequencies based on the fluid to be measured and a specific parameter that may be the focus of detection.

The example implementation described takes advantage of a constant voltage source exciting the cell circuit. It is also possible to construct a complementary system where the cell is driven by a constant current source and measurements made with a current measurement device.

In some implementations, the data collecting cell is a conductivity cell.

In some implementations, the data collecting cell includes two electrodes.

In some implementations, the data collecting cell includes an inlet and an outlet, wherein the medical fluid enters the data collecting cell through the inlet and flows out of the data collecting cell through the outlet.

In some implementations, the data collecting cell is calibrated for a specific cell constant that is determined based at least in part on locations of two electrodes of the data collecting cell with respect to each other.

In some implementations, the data collecting cell is calibrated for a specific cell constant that is determined based on the dimensions of the two electrodes.

In some implementations, the data collecting cell is calibrated for a specific cell constant that is determined based on the conductive material make-up of the two electrodes.

In some implementations, the circuit is configured to be attached to a dialysis system.

In some implementations, the dialysis system includes a peritoneal dialysis machine.

In some implementations, the medical fluid includes dialysate or saline.

Devices and methods in accordance with the present disclosure may include any combination of the aspects and features described herein. That is, devices in accordance with the present disclosure are not limited to the combinations of aspects and features specifically described herein, but also include any combination of the aspects and features provided.

Implementations of the present disclosure provide one or more of the following technical advantages and/or technical improvements over previously available solutions. The implementations allow monitoring fluid parameters (e.g., concentration, fluid elements, etc.) of a medical fluid by measuring electrical characteristics of the fluid. For example, a dialysate should have a conductivity that indicates that a certain amount and ratio of sodium bicarbonate is present, because an imbalance could impact the health of the patient and cause discomfort. The present implementations provide a sensor technique that can measure conductivity of the dialysate to determine patient treatment parameters without making direct contact (e.g., via electrodes) with the patient's body.

In some implementations, the devices, systems, methods, and techniques described herein can provide a number of additional advantages. For example, in some implementations, measuring conductivity using the techniques described herein allows for quick, accurate conductivity measurements without requiring calibration of the data collecting system. That is, the data collecting system which drives and interacts with the cell need not be calibrated ahead of time (e.g., prior to conductivity measurements being taken) because any errors included in the circuit are canceled out by common mode voltage measurement techniques described herein. In this way, the data collecting system may be said to be "self-calibrating." Because calibration is not required, quicker measurements can be taken as compared to measurements taken by data collecting systems that require calibration ahead of time or in real time.

The cell constant is premeasured and known ahead of time which is set by the size, material of the electrodes and spacing of the electrodes. So long as these parameters do not change, the cell constant will remain constant.

Further, the data collecting system and the associated techniques described herein present no phase shift issues because the applied AC voltages and currents are essentially being rectified (e.g., such that they are converted to DC). In this way, the waveform is essentially integrated. In particular, any phase angle shift in the AC current from the AC voltage can be integrated out over time to steady state (e.g., DC) voltage and current values. Because patient parameters do not change instantaneously, instantaneous measurement of conductivity is not required thereby allowing the departure from conventional AC measurement techniques which required phase alignment and compensation in calculations. The details of one or more implementations of the present disclosure are set forth in the accompanying drawings and the description below. Other features and advantages of the present disclosure will be apparent from the description and drawings, and from the claims.

DESCRIPTION OF DRAWINGS

Like reference symbols in the various drawings indicate like elements.

DETAILED DESCRIPTION

Implementations of the present disclosure provide a device that can be used to measure one or more electrical characteristics (e.g., electrical conductivity) of fluids in dialysis systems. The device has a data collecting cell that includes a chamber with an inlet and an outlet. Fluid enters the chamber through the inlet and flows out of the chamber through the outlet. Multiple electrodes (e.g., two electrodes) are located within the chamber to measure electrical characteristics of the fluid.

Implementations of the present disclosure also provide a circuit for measuring electrical characteristics (e.g., electrical conductivity) of fluid flowing through a data collecting cell (e.g., a conductivity cell). The circuit can accurately measure the conductivity of the fluid without requiring calibration, as described in more detail below. Thus, measurement systems can be easily employed without calibration and without sacrificing the accuracy of the measurements.

Figure 1:
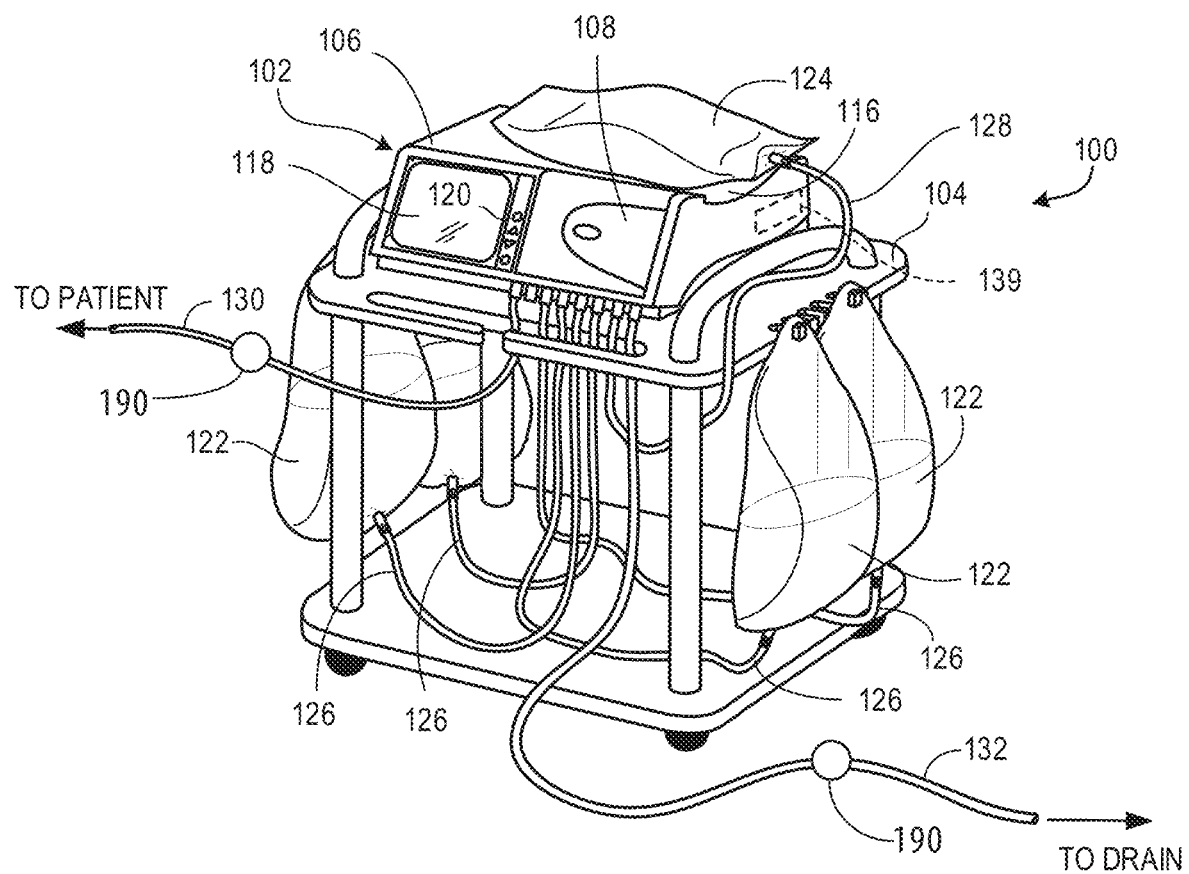
FIG. 1 illustrates an example of a peritoneal dialysis (PD) system with example placement of data collection cell positions.

In general, the data collecting cell may be part of a medical system, such as a dialysis system (e.g., a peritoneal dialysis system, a hemodialysis system, etc.) or another type of medical systems such as a heart-lung system, a chemotherapy system, etc. Medical fluid flowing through the medical system and/or medical fluid flowing to and/or from the patient may flow through the data collection cell such that one or more properties of the medical fluid can be measured. FIG. 1 shows an example of a medical system in which the data collecting cell may be implemented. In particular, FIG. 1 shows an example peritoneal dialysis system 100, although it should be understood that the data collecting cell may be implemented in other types of medical systems. In the illustrated example, the peritoneal dialysis system 100 includes a PD machine (also generally referred to as a PD cycler) 102 seated on a cart 104. The PD machine 102 includes a housing 106, a door 108, and a cassette interface 110 that contacts a disposable PD cassette 112 when the cassette 112 is disposed within a cassette compartment 114 formed between the cassette interface 110 and the closed door 108. A heater tray 116 is positioned on top of the housing 106. The heater tray 116 is sized and shaped to accommodate a bag of PD solution such as dialysate (e.g., a 5 liter bag of dialysate). The PD machine 102 also includes a user interface such as a touch screen display 118 and additional control buttons 120 that can be operated by a user (e.g., a caregiver or a patient) to allow, for example, set up, initiation, and/or termination of a PD treatment.

Dialysate bags 122 are suspended from fingers on the sides of the cart 104, and a heater bag 124 is positioned in the heater tray 116. The dialysate bags 122 and the heater bag 124 are connected to the cassette 112 via dialysate bag lines 126 and a heater bag line 128, respectively. The dialysate bag lines 126 can be used to pass dialysate from dialysate bags 122 to the cassette 112 during use, and the heater bag line 128 can be used to pass dialysate back and forth between the cassette 112 and the heater bag 124 during use. In addition, a patient line 130 and a drain line 132 are connected to the cassette 112. The patient line 130 can be connected to a patient's abdomen via a catheter and can be used to pass dialysate back and forth between the cassette and the patient's peritoneal cavity during use. This location is one position where a data collecting cell 190 can be located to evaluate the difference in the conductivity of fluid entering the patient to the fluid exiting the patient. The catheter may be connected to the patient line 130 via a port such as a fitting. The drain line 132 can be connected to a drain or drain receptacle and can be used to pass dialysate from the cassette 112 to the drain or drain receptacle during use. Line 132 in another location for a data collecting cell 190 to measure conductivity in the fluid being drained from the system. It should be understood that the two example positions for the data collecting cell listed in this paragraph are not exclusive. Such cells could be located in any of the lines.

The PD machine 102 also includes a control unit 139 (e.g., a processor). The control unit 139 can receive signals from and transmit signals to the touch screen display 118, the control panel 120, and the various other components of the PD system 100. The control unit 139 can control the operating parameters of the PD machine 102. In some implementations, the control unit 139 is an MPC823 PowerPC device manufactured by Motorola, Inc.

Figure 2:
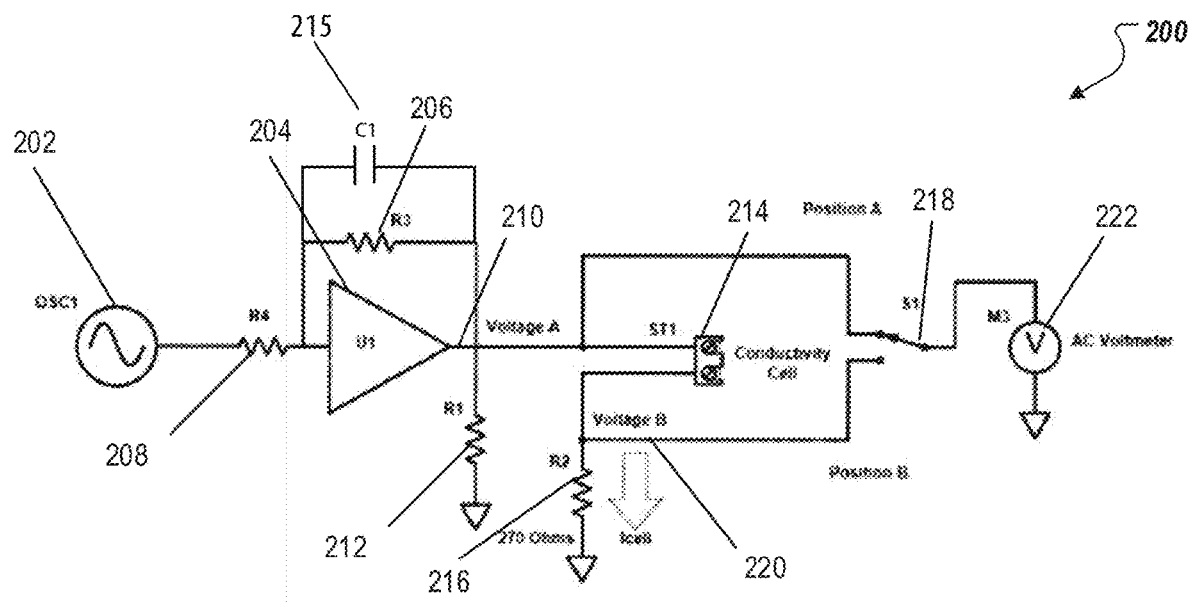
FIG. 2 illustrates an example measurement circuit for connection to a data collection cell to determine the conductivity of fluid flowing through a data collecting cell.

A data collecting cell with measurement system can be implemented in the medical system. With the presented implementations, the data collecting cell may be implemented in a way such that calibration of the data collecting cell measurement system is not required to yield accurate measurements. An example data collecting cell measurement system is shown in FIG. 2. In particular, FIG. 2 shows an example circuit 200 that can be used to measure the conductivity of the fluid flowing through the data collecting cell. Measurements can be obtained using a "common mode" technique, as described in detail below. By utilizing common mode DC measurement techniques, phase angle shifts in AC current from AC voltage can be integrated out over time (e.g., over a few milliseconds) to steady state voltage and current values. In turn, various factors (e.g., that would otherwise need to be considered and accounted for using other measurement techniques) can be ignored because they essentially divide out from the calculation. For example, characteristics of the electrode posts (e.g., the material they are made of) need not be considered because any effects are equally present across the measurements.

In general, an excitation voltage (e.g., a fixed excitation voltage) or an excitation current (e.g. a fixed excitation current) is applied to the data collecting cell. For a fixed voltage excitation, current through the data collecting cell is measured. For a fixed current excitation, voltage across the data collecting cell is measured. In some implementations, two electrodes may provide the excitation, and the same two electrodes may be used to measure the resultant parameter. Circuit 200 in FIG. 2 provides an illustrated example implementation of a measurement circuit which uses voltage excitation.

It should be understood that the circuit 200 includes various components that are used to tune the excitation voltage and such components are described with respect to FIG. 2 for illustrative purposes only. Other components having various values and/or placements may be added to, removed from, or swapped from the circuit 200 without departing from the spirit and scope of the inventive concepts described herein.

In the illustrated example implementation, the circuit 200 includes an input frequency source 202 with an alternating current (AC) output. In some implementations, the input frequency source 202 is configured to provide a wave having sinusoidal properties (e.g., a sine wave). In some implementations, additional components may be connected to the input frequency source 202 to cause the voltage waveform to have sinusoidal properties. For example, in some implementations, a frequency source 202 producing a square wave output can be filtered with an additional series resistor between frequency source 202 and resistor R4 208 and an additional capacitor to ground from the junction of the added resistor and resistor R4 208. The values of the added resistor and capacitor are adjusted to create a triangle waveform from the square wave output of frequency source 202 with near sinusoidal properties. In some implementations, the input frequency source 202 operates at a frequency of about 100 kHz.

The input voltage source 202 is provided to an op-amp 204. In the illustrated example, the op-amp 204 provides a fixed voltage excitation source to the data collecting cell connected at 214. In the illustrated example, the gain of the op-amp 204 is established by the ratio of R3 206 divided by R4 208. In the illustrated example, values for R3 206 relative to R4 208 are chosen such that an output voltage of the op-amp 204 (e.g., Voltage A 210) is a constant voltage such as +/−2 Vp-p. In some implementations (e.g., depending on one or more characteristics of the op-amp 204 and the value of R3 206), the op-amp 204 is compensated with a particular capacitor value of C1 215 such that the frequency response is sufficient for passing 100 kHz. In some implementations, capacitor value C1 215 may be adjusted to make the waveform more sinusoidal. To optimize phase margin to ensure stability (i.e., non-oscillation of the op-amp 204) in the circuit 200, the ratio of R3 206 divided by R4 208 may be maintained close to unity (e.g. 1). In an op-amp circuit, this ratio of the feedback resistor R3 206 divided by the input resistor R4 208 is the pass-band gain of the op-amp. In some implementations, the input AC voltage source 202 is provided by a microcontroller that may have a 5V supply (resulting in an AC voltage swing of +/−2.5V when capacitively coupled to circuit 200) or a 3V supply (resulting in an AC voltage swing of +/−1.5V when capacitively coupled to circuit 200). Because the output impedance of the op-amp 204 is very low (e.g., on the order of 20 Ohms or less), the output voltage of op-amp 204 emulates a constant voltage source. In some implementations, R1 212 provides a reference output load for op-amp 204 to maintain op-amp output characteristics of Voltage A 210 and minimize load transients during measurements. Though not critical in value, the illustrated example R1 212 has a value of 4.7 k Ohms, sinking a minimal current of approximately 0.4 mA.

Figure 3:
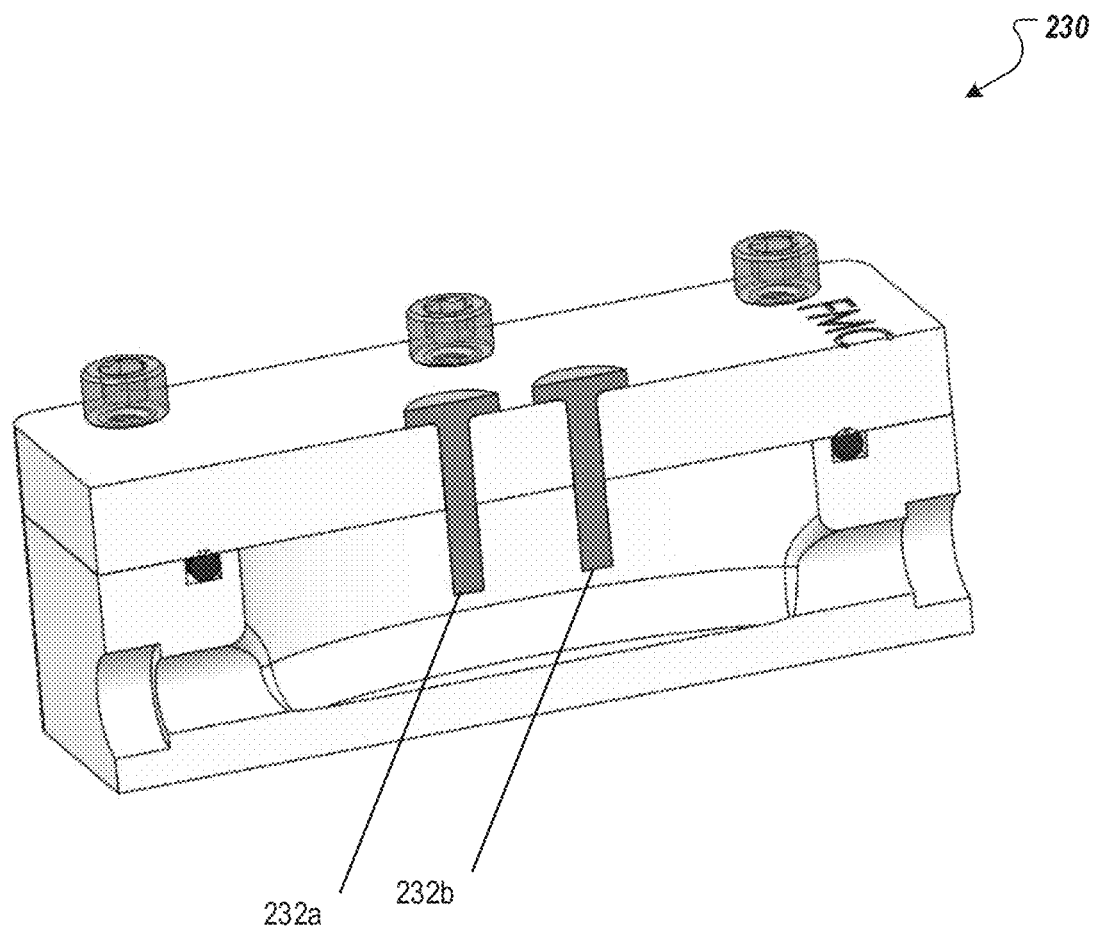
FIG. 3 illustrates an example cross section of a data collecting cell.

For the illustrated example, a two-post data collecting cell 230 of FIG. 3 (or another similar data collecting cell) is connected at 214 of the measurement circuit 200 in FIG. 2. One post 232a of the data collecting cell 230 in FIG. 3 is connected to Voltage A 210 through a first connection at 214 of FIG. 2. The other post 232b of the data collecting cell 230 in FIG. 3 is connected to a fixed precision resistor R2 216 through a second connection at 214 of FIG. 2.

The current path Icell for measurement of conductivity by circuit 200 in FIG. 2 of the fluid in the data collecting cell 230 in FIG. 3 is from the fixed excitation Voltage A 210 through a first connection at 214 in FIG. 2; to a pin such as 232a in conductivity cell 230 in FIG. 3; through the fluid in the data collecting cell 230 flowing between posts 232a and 232b in FIG. 3; from post 232b of 230 in FIG. 3 to a second connection of 214 in FIG. 2; through a precision resistor R2 216 in FIG. 2 to ground potential. It is noted that the post connections 232a, 232b of the data collection cell 230 in FIG. 3 are interchangeable. It is also noted that connector 214 in FIG. 2 is for convenience in connecting the data collection cell 230 in FIG. 3. It is not required if the data collection cell 232 posts 232a, 232b in FIG. 3 are directly connected to Voltage A 210 and R2 216 in FIG. 2. For brevity, the data collection cell will hereafter be referred to as 214 even though these are convenient connection points for the conductivity cell. The value for R2 216 may be chosen based on the conductivity values expected to be measured by the circuit 200 for improved resolution of a measurement device. In the illustrated example, R2 216 has a value of 270 Ohms to optimize resolution of expected measured conductivity values in the 13.5 mS/cm to 14 mS/cm range. Different values for R2 may be used to provide the best resolution at a different conductivity range of interest.

In order to measure the conductance of the fluid in the data collection cell connected at 214, Voltage A 210 and the voltage across R2 216 (e.g., Voltage B 220) are required. Such voltage measurements are made by a voltage measurement unit such as an alternating current (AC) voltmeter 222 that is connected to a switch 218. The switch 218 provides for easy switching of the AC voltmeter 222 between measurements of Voltage A 210 and Voltage B 220. The AC voltmeter 222 must have a high enough input impedance such that the conductivity of the data collection cell in series with resistor R2 216 are not loaded. The AC voltmeter 222 does not result in loading of the measurement circuit such as to modify the measurements being made.

The switch 218 is configured to switch between a first state in which the AC voltmeter 222 is configured to measure Voltage A 210 (e.g., the input voltage to the data collection cell 214) and a second state in which the AC voltmeter 222 is configured to measure Voltage B 220 (e.g., the output voltage of the data collection cell 214). The voltage across the data collection cell 214 is found by measuring Voltage A 210 at the top of the conductivity cell 214 (e.g., the input voltage) and Voltage B 220 at the bottom of the conductivity cell 214 (e.g., the output voltage) and subtracting:

$$\text{Data Collection Cell Voltage} = \text{Voltage } A - \text{Voltage } B \quad \text{Equation (1)}$$

By using the same AC voltmeter 222 to measure both Voltage A 210 and Voltage B 220, the measurements are made in "common mode." As such, any calibration error in the AC voltmeter 222 will appear in both Voltage A 210 and Voltage B 220, and will subsequently divide out as will be illustrated in the below equations.

The current through the data collection cell 214 is the same as the current through the series resistor R2 216. Thus, the current is:

$$\text{Data Collection Cell Current} = \text{Voltage } B/270 \text{ Ohms} \quad \text{Equation (2)}$$

The conductance of the fluid in the data collection cell 214 is then found by dividing the cell current by the cell voltage:

$$\text{Data Collection Cell Fluid Conductance} = \text{Cell Current}/\text{Cell Voltage} \quad \text{Equation (3)}$$

Conductivity is then determined by multiplying the data collection cell fluid conductance by the data collection cell constant, which is determined by measuring known solutions in the conductivity circuit 200. In some implementations, the conductivity cell 214 "cell constant," which relates the sensor posts 232a and 232b in the fluid, is pre-calibrated. That is, the cell constant for the data collection cell 214 with sensor posts connected to the terminals (e.g., sometimes collectively referred to herein as the electrodes) may be determined ahead of time such that the conductivity can be determined without further calibration being required. The data collection cell constant is a function of the data collection cell 230 geometry, placement of the sensor posts 232a and 232b within the data collection cell 230 and properties of the sensor posts 232a and 232b. If manufactured through molding and/or other tight tolerance methods, the data collection cell constant should be as its name indicates—a constant. Therefore:

$$\text{Conductivity} = \text{Data Collection Cell conductance} \times \text{Data Collection Cell constant} \quad \text{Equation (4)}$$

The circuit 200 can be used to measure the conductivity without calibrating the system (e.g., the circuit 200). For example, so long as the AC voltmeter 222 is stable over the time of the Voltage A 210 and Voltage B 220 measurements, then specific calibration of the circuit 200 is not required. To illustrate this aspect, consider Condition 1 in which all components and calibrations are perfect. The resulting measurements are:

$$V \text{ Data Collection Cell Perfect} = \text{Voltage } A \text{ Perfect} - \text{Voltage } B \text{ Perfect} \quad \text{Equation (5)}$$

$$I \text{ Data Collection Cell Perfect} = \text{Voltage } B \text{ Perfect}/270 \text{ Ohms} \quad \text{Equation (6)}$$

$$\text{Data Collection Cell Conductance Perfect} = I\text{cell Perfect}/V\text{cell Perfect} \quad \text{Equation (7)}$$

Now consider a Condition 2 example in which the AC voltmeter 222 is out of calibration by a gain error of 20% to the positive (e.g., Vac=Vperfect*1.2) during the time period of the measurements. Then the following analysis applies:

$$V \text{ Data Collection Cell} = 1.2^*\text{Voltage } A \text{ Perfect} - 1.2^*\text{Voltage } B \text{ Perfect} \quad \text{Equation (8)}$$

$$I \text{ Data Collection Cell} = 1.2^*\text{Voltage } B \text{ Perfect}/270 \text{ Ohms} = 1.2^*(I\text{cell Perfect}) \quad \text{Equation (9)}$$

$$\text{Data Collection Cell Conductance} = I\text{cell}/V\text{cell} = (1.2^*I\text{cell Perfect}/[1.2^*(\text{Voltage } A \text{ Perfect} - \text{Voltage } B \text{ Perfect})] = I\text{cell Perfect}/V\text{cell Perfect} \quad \text{Equation (10)}$$

Under Condition 2, the 1.2 factor divides out due to using the common mode of measurement with the same AC voltmeter 222. Therefore, no calibration of the AC voltmeter 222, the conductivity cell 230 or the other components of the circuit 200 is required.

A similar analysis can be performed for the condition if Voltage A 210 changes slightly. So long as the change is constant during the time window when the measurements of Voltage A 210 and Voltage B 220 are made, then this change also divides out of the conductance calculations and no calibration of the circuit 200 is required.

The circuit 200 described with respect to FIG. 2 can provide a number of advantages. In some implementations, measuring conductivity using the techniques described herein allows for quick, accurate conductivity measurements without requiring calibration of the data collecting cell 230. That is, the data collecting cell 230 need only be calibrated once ahead of time to establish the conductance to conductivity cell constant. Once known, so long as the data collection cell 230 is manufactured the same way with the same dimensions and materials, all that is required is an accurate conductance measurement by the measurement circuit 200. Because any errors included in the conductance measurement circuit 200 are canceled out by the common mode voltage measurement techniques described in this example embodiment and the data collection cell can be uniformly manufactured to produce a fixed, repeatable conductance to conductivity conversion factor, this composite conductivity measurement system may be said to be "self-calibrating". Because calibration is not required, quicker measurements can be taken as compared to measurements taken by data collecting cells that require calibration ahead of time or in real time.

Further, the data collecting cell 230 and the associated techniques described herein present no phase shift issues because the applied AC voltage and current are being rectified (e.g., such that they are converted to DC). In this way, the AC waveform is largely integrated. Further, any phase angle shift in the AC current from the AC voltage can be integrated out over time to steady state (e.g., DC) voltage and current values. In other words, since instantaneous measurement of conductivity rarely (if ever) required, through facilitating a short integration time for the voltage and current measurements and DC analysis, the complexity and inaccuracies of making phase-corrected AC measurements are overcome. The result is a measurement circuit that can obtain measurements quicker (e.g., because calibration is not required), which is simpler, and which is lower cost.

Figure 4:
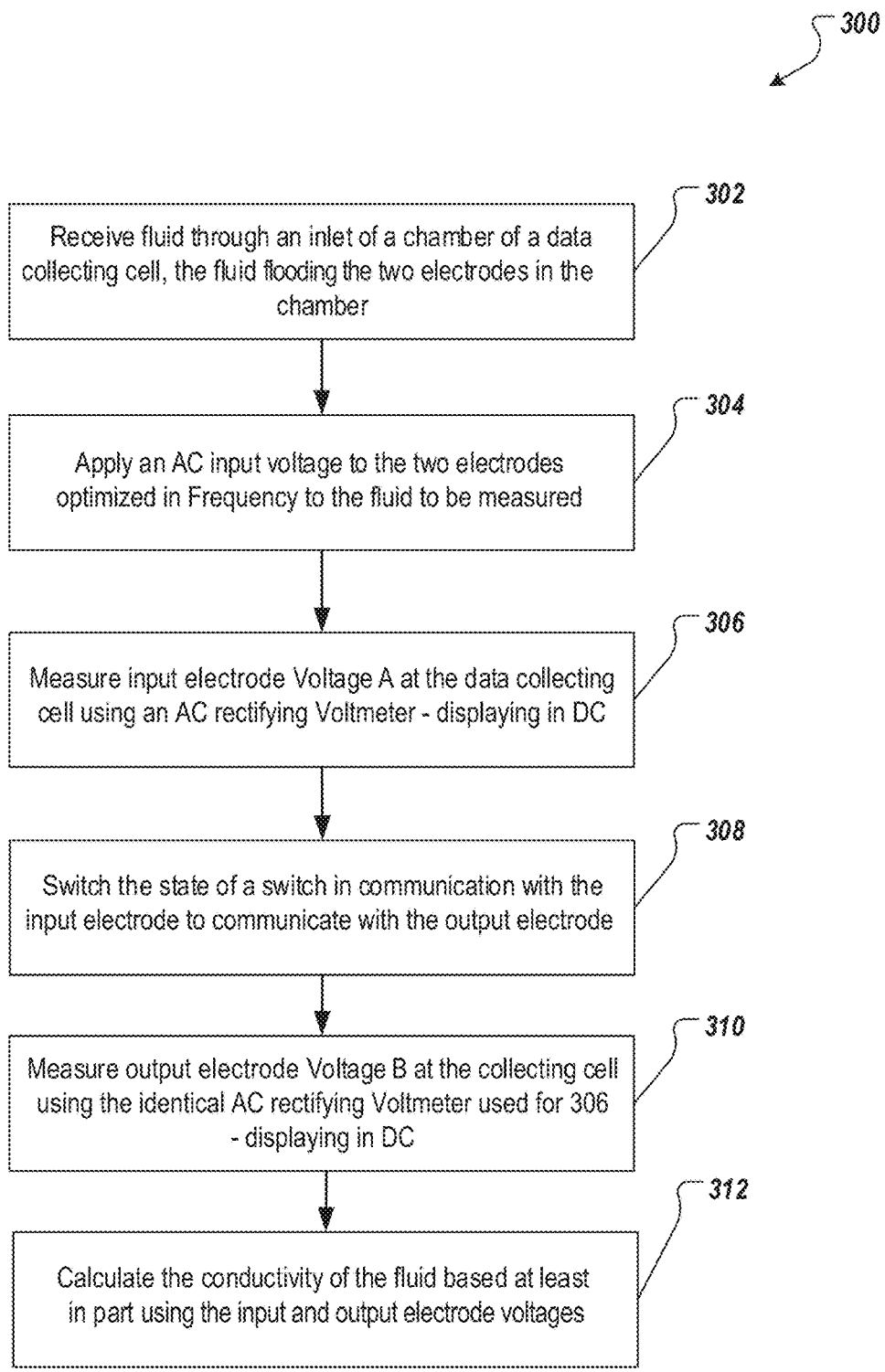
FIG. 4 depicts an example process that can be executed in accordance with the implementations described herein.

The procedure disclosed for making measurements can be manually made or automated. FIG. 4 depicts an example process 300 that can be executed in accordance with the implementations of the present disclosure. The process 300 can be implemented by a medical system, such as a dialysis system (e.g., the PD system 100), or another type of medical system that includes the data collecting cells described herein.

In this process, fluid is received through an inlet of a chamber of the data collecting cell, and flows about two electrodes located within the chamber (302). For example, fluid can be received at a chamber of the data collecting cell through an inlet.

An input voltage is applied to the data collecting cell (304). For example, an input voltage source can provide an input voltage to the electrodes of the data collecting cell.

A voltage measurement unit is configured to measure the input voltage and the output voltage at the electrodes. The voltage measurement unit may be an AC voltage measurement unit with a high impedance input (so as not to load the measurement) which rectifies and integrates the voltage to DC. A switch is in communication with the voltage measurement unit. When the switch switches states 308, the voltage measurement unit switches from measuring the input voltage of the data collecting cell 306 and an output voltage of the data collecting cell 310. The input voltage is measured at one of the electrodes of the data collecting cell 306, and the output voltage is measured at the other electrode of the data collecting cell 310, as described in detail above. First, the input voltage is measured (306). The switch then switches states (308), and the output voltage is measured (310).

Using at least the measured input voltage and output voltage, various calculations are performed to determine the conductance and conductivity of the medical fluid (312), as described in detail above. For example, a cell voltage is determined by taking a difference between the input voltage and the output voltage, and a cell current is determined by measuring a current through a resistor connected to the data collecting cell output. A cell conductance is determined by dividing the cell current by the cell voltage, and the conductivity is determined by multiplying the cell conductance by a cell constant (e.g., a previously-determined cell constant). Measuring the conductivity using this technique requires no calibration of the data collecting cell or the voltage measurement unit.

Figure 5:
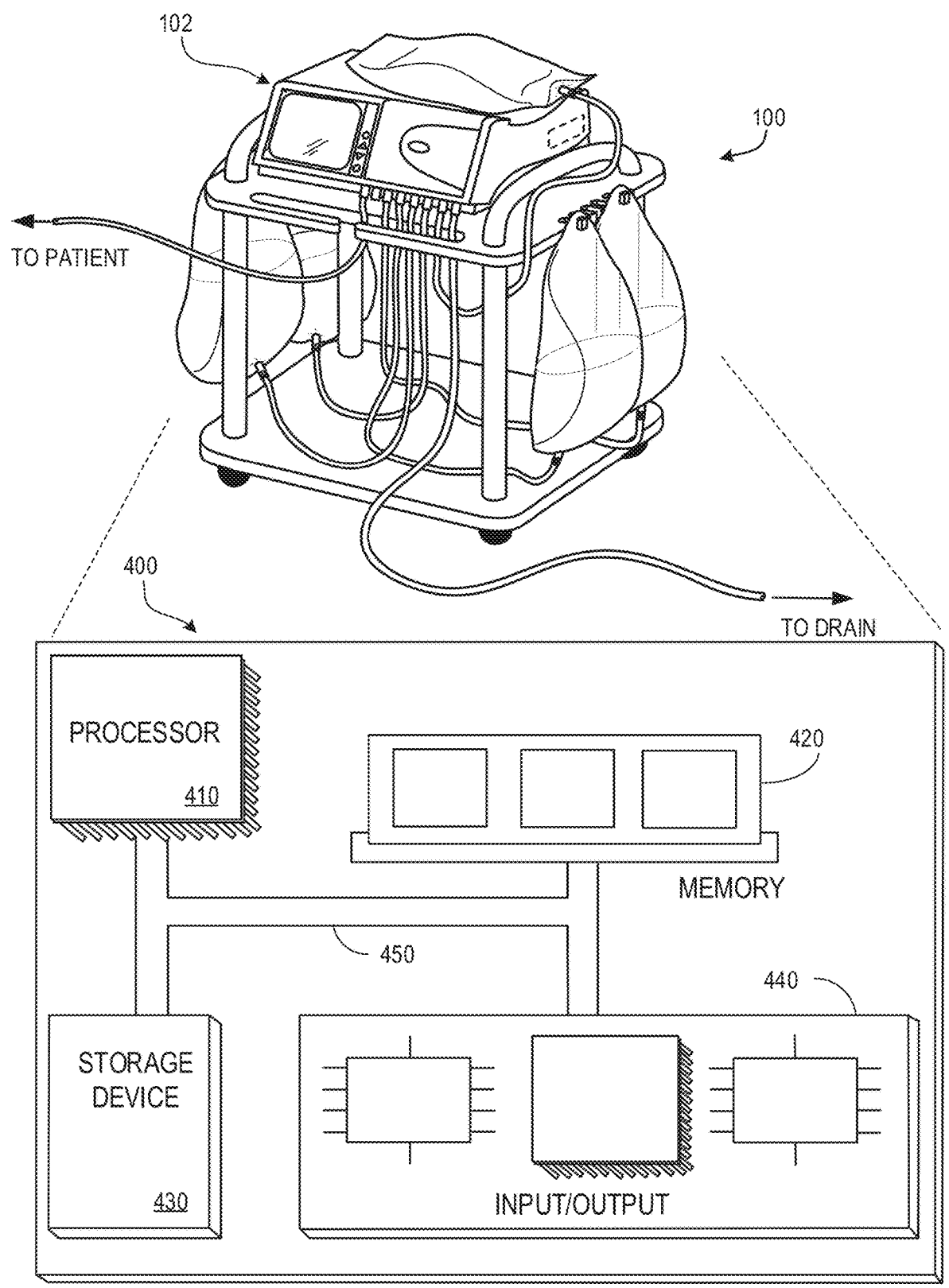
FIG. 5 shows an example of a computer system and related components that can be used to automate the implementation of the techniques described herein.

FIG. 5 is a block diagram of an example computer system 400 that can be used as part of a medical systems described herein, for example, to perform measurements and/or analyses related to the data collecting cell. A control unit, such as a computing device and/or a microcontroller, could be examples of the system processor 410 described here. The measurement unit and/or the data collecting unit described herein can be part of any medical system, such as dialysis systems (e.g., a hemodialysis system), a heart lung machine, a chemotherapy system, or any other system that introduces fluid into body.

The system 400 includes a processor 410, a memory 420, a storage device 430, and an input/output device 440. Each of the components 410, 420, 430, and 440 can be interconnected, for example, using a system bus 450. The processor 410 is capable of processing instructions for execution within the system 400. The processor 410 can be a single-threaded processor, a multi-threaded processor, or a quantum computer. The processor 410 is capable of processing instructions stored in the memory 420 or on the storage device 430. The processor 410 may a shared processor with a host system (such as a dialysis or PD system) which may also execute conductivity measurements.

The memory 420 stores information within the system 400. In some implementations, the memory 420 is a computer-readable medium. The memory 420 can, for example, be a volatile memory unit or a non-volatile memory unit. In some implementations, the memory 420 stores information for causing the pumps of the dialysis system to operate as described herein.

The storage device 430 is capable of providing mass storage for the system 400. In some implementations, the storage device 430 is a non-transitory computer-readable medium. The storage device 430 can include, for example, a hard disk device, an optical disk device, a solid-date drive, a flash drive, magnetic tape, or some other large capacity storage device. The storage device 430 may alternatively be a cloud storage device, e.g., a logical storage device including multiple physical storage devices distributed on a network and accessed using a network.

In an alternate example of implementation, the processing system 400 can be stand-alone to perform the conductivity measurements and interface via the input/output sub-system 440 with a similar input/output system of a host medical device to pass resulting conductivity data. In this example of implementation, the processing system 400 can be a stand-alone system which includes controls and a display interfaced to the input/output sub-system 440. In some implementations, the system 400 is a microcontroller. A microcontroller is a device that contains multiple elements of a computer system in a single electronics package. For example, the single electronics package could contain the processor 410, the memory 420, the storage device 430, and input/output devices 440.

The input/output device 440 provides input/output operations for the system 400. In some implementations, the input/output device 440 includes one or more of network interface devices (e.g., an Ethernet card), a serial communication device (e.g., an RS-232 10 port), and/or a wireless interface device (e.g., an 802.11 card, a 3G wireless modem, or a 4G wireless modem). In some implementations, the input/output device 440 may include short-range wireless transmission and receiving components, such as Wi-Fi, Bluetooth, and/or near field communication (NFC) components, among others. In some implementations, the input/output device includes driver devices configured to receive input data and send output data to other input/output devices, e.g., keyboard, printer and display devices (such as a touch screen display). In some implementations, mobile computing devices, mobile communication devices, and other devices are used. In some implementations, the input/output devices can be configured with drivers to complete the measurement steps and configurations of the conductivity circuit shown in FIG. 4.

While dialysate was used herein as an example fluid for describing the functionality of the embodiments, the data collecting unit, in general, and the data collecting cell, in particular, can be used for determining electrical characteristics of any other type of fluid, for example, fluids in which conductivity changes with a biological parameter. Examples of medical fluids include blood, effluent PD drainage, plasma, saline, and urine, to name a few.

A number of embodiments of the invention have been described. Nevertheless, it will be understood that various modifications may be made without departing from the spirit and scope of the invention. Accordingly, other embodiments are within the scope of the following claims.

What is claimed is:

1. A circuit for measuring the conductivity of a medical fluid, the circuit comprising:
   a data collecting cell through which a medical fluid is configured to flow;
   an input voltage source that provides an input voltage to the data collecting cell;
   a voltage measurement unit configured to measure the input voltage and an output voltage of the data collecting cell; and
   a switch in communication with the voltage measurement unit, the switch configured to switch between a first state in which the voltage measurement unit is configured to measure the input voltage and a second state in which the voltage measurement unit is configured to measure the output voltage of the data collecting cell, wherein a cell current is determined by measuring a current through a resistor connected to an output of the data collecting cell.

2. The circuit of claim 1, wherein a cell voltage is determined by taking a difference between the input voltage and the output voltage.

3. The circuit of claim 2, wherein a cell conductance is determined by dividing the cell current by the cell voltage.

4. The circuit of claim 3, wherein the conductivity of the medical fluid flowing through the data collecting cell is determined by multiplying the cell conductance by a cell constant.

5. The circuit of claim 4, wherein the cell constant is determined by measuring one or more conductivities of known solutions by the circuit.

6. The circuit of claim 5, wherein the cell constant is pre-calibrated such that the cell constant is known before the conductivity of the medical fluid is measured.

7. The circuit of claim 3, wherein calibration of the voltage measurement unit is not required to provide an accurate measurement of the cell conductance.

8. The circuit of claim 1, wherein the input voltage source operates at a frequency of about 100 kHz.

9. The circuit of claim 1, further comprising one or more capacitors and one or more resistors in electrical communication with the input voltage source for defining properties of the input voltage.

10. The circuit of claim 1, wherein the data collecting cell is a conductivity cell.

11. The circuit of claim 1, wherein the data collecting cell includes two electrodes.

12. The circuit of claim 1, wherein the data collecting cell includes an inlet and an outlet, wherein the medical fluid enters the data collecting cell through the inlet and flows out of the data collecting cell through the outlet.

13. The circuit of claim 1, wherein the data collecting cell is calibrated for a specific cell constant that is determined based at least in part on locations of two electrodes of the data collecting cell with respect to each other.

14. The circuit of claim 1, wherein the circuit is configured to be attached to a dialysis system.

15. The circuit of claim 14, wherein the dialysis system includes a peritoneal dialysis machine.

16. The circuit of claim 1, wherein the medical fluid comprises dialysate or saline.

* * * * *